(12) United States Patent
LeJeune

(10) Patent No.: US 8,186,353 B1
(45) Date of Patent: May 29, 2012

(54) EMERGENCY TRACHEOTOMY TUBE AND PACKAGE

(76) Inventor: Francis E. LeJeune, River Ridge, LA (US)

( * ) Notice: Subject to any disclaimer, the term of this patent is extended or adjusted under 35 U.S.C. 154(b) by 608 days.

(21) Appl. No.: 12/369,439

(22) Filed: Feb. 11, 2009

Related U.S. Application Data

(60) Provisional application No. 61/027,706, filed on Feb. 11, 2008.

(51) Int. Cl.
*A61M 16/00* (2006.01)
(52) U.S. Cl. .......... 128/207.29; 128/207.14; 128/207.17
(58) Field of Classification Search .......... 128/207.14–207.17, 207.29
See application file for complete search history.

(56) References Cited

U.S. PATENT DOCUMENTS

| | | | |
|---|---|---|---|
| 460,987 A * | 10/1891 | Olivieri | 128/207.14 |
| 3,306,297 A | 2/1967 | Voorhees et al. | |
| 3,415,250 A * | 12/1968 | Peterson | 128/207.29 |
| 3,511,243 A | 5/1970 | Toy | |
| 3,802,428 A | 4/1974 | Sherman | |
| 4,332,245 A | 6/1982 | Boone, Sr. | |
| 4,632,112 A | 12/1986 | Matthews | |
| 5,546,939 A | 8/1996 | French | |
| 5,671,732 A | 9/1997 | Bowen | |
| 6,637,435 B2 * | 10/2003 | Ciaglia et al. | 128/207.29 |
| 7,267,124 B1 | 9/2007 | Roberson, Jr. et al. | |
| 7,552,732 B2 * | 6/2009 | Newman | 128/207.15 |

* cited by examiner

*Primary Examiner* — Lynne Anderson
(74) *Attorney, Agent, or Firm* — Garvey, Smith, Nehrbass & North, L.L.C.; Charles C. Garvey, Jr.; Vanessa M. D'Souza

(57) ABSTRACT

A tracheotomy tube apparatus that can be contained in a generally flat or collapsed condition for easy transport in a purse or wallet provides a planar sheet member having upper and lower surfaces, the sheet member being flexible so that it can be formed into a tracheal tube shape. The sheet member includes a flange that has a connector for attaching it to the neck area of a patient. The flange can be fitted with a string or cable that can be used to encircle the patients neck and tie the flange to the patients neck. The kit can include a generally flat package that contains the planar sheet member and a small disposable cutting instrument or scalpel. During use, the planar sheet member provides a section that is curled or rolled into the shape of a cone or tube that can be placed into a surgically formed opening in the patients trachea. The flange holds the formed tracheal tube in the selected position. The flange can be affixed to the patients neck using a string or cable that can be provided as part of the kit.

20 Claims, 2 Drawing Sheets

EMERGENCY TRACHEOTOMY TUBE AND PACKAGE

CROSS-REFERENCE TO RELATED APPLICATIONS

Priority of U.S. Provisional Patent Application Ser. No. 61/027,706, filed Feb. 11, 2008, incorporated herein by reference, is hereby claimed.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The present invention relates to tracheotomy tubes and more particularly to a portable, emergency tracheotomy tube apparatus that is packaged in a generally flat condition so that it can be carried easily in a wallet or purse of a physician for immediate use in case of an emergency. More particularly, the present invention relates to a tracheotomy tube apparatus wherein the tracheotomy tube is in the form of a planar or flat sheet member having upper and lower surfaces, the sheet being flexible so that it can be formed into a tracheal tube shape, a flange being attached to the sheet member, the flange having a securement device for attaching the flange to the neck of a patient during use.

2. General Background of the Invention

Several different types of tracheal tubes have been patented. The following table provides examples of such patents.

The following U.S. patents are incorporated herein by reference:

TABLE

| U.S. Pat. No. | TITLE | ISSUE DATE |
| --- | --- | --- |
| 3,306,297 | Tracheotomy Set | Feb. 28, 1967 |
| 3,511,243 | Apparatus for Providing a Breathing Conduit Communicating with the Trachea at the Base of the Neck | May 12, 1970 |
| 3,802,428 | Disposable Device for Applying Mouth to Mouth Resuscitation | Apr. 09, 1974 |
| 4,332,245 | Emergency Trachea Airway | Jun. 01, 1982 |
| 4,632,112 | Procedure for Draining Fluid from Lungs | Dec. 30, 1986 |
| 5,546,939 | Emergency Tracheostomy Apparatus | Aug. 20, 1996 |
| 5,671,732 | Tracheostomy Tube Holder | Sep. 30, 1997 |
| 7,267,124 | Emergency Tracheostomy Kit | Sep. 11, 2007 |

Unfortunately, people often are placed in an emergency situation when food lodges in their windpipe or trachea and prevents normal breathing. Such an unfortunate situation can occur in an area that is far from a hospital or from emergency care. Even if a surgeon is present, the surgeon may not be able to help the patient without having a tracheotomy tube, scalpel or other instruments that would help open an airway for the person having an obstructed trachea.

BRIEF SUMMARY OF THE INVENTION

The present invention solves the prior art problems by providing a tracheotomy tube apparatus that can be packaged in a flat or generally flat condition. Such a conveniently packaged tracheotomy tube apparatus could be quickly produced by a surgeon who is carrying one in a wallet or purse.

The present invention provides an improved tracheotomy tube apparatus that includes a planar sheet member having upper and lower surfaces, the sheet member being flexible so that it can be formed into a tracheal tube shape.

The sheet member provides a flange that can be fitted with a string, rope, cable or adhesive for attaching the flange to the patients neck area, for securing it in the proper position next to a surgically formed opening. The kit could also contain a disposable scalpel or like cutting instrument that would enable the surgeon to quickly form an airway into which is placed the improved tracheotomy tube apparatus of the present invention.

BRIEF DESCRIPTION OF THE SEVERAL VIEWS OF THE DRAWINGS

For a further understanding of the nature, objects, and advantages of the present invention, reference should be had to the following detailed description, read in conjunction with the following drawings, wherein like reference numerals denote like elements and wherein.

DETAILED DESCRIPTION OF THE INVENTION

Figure 1:
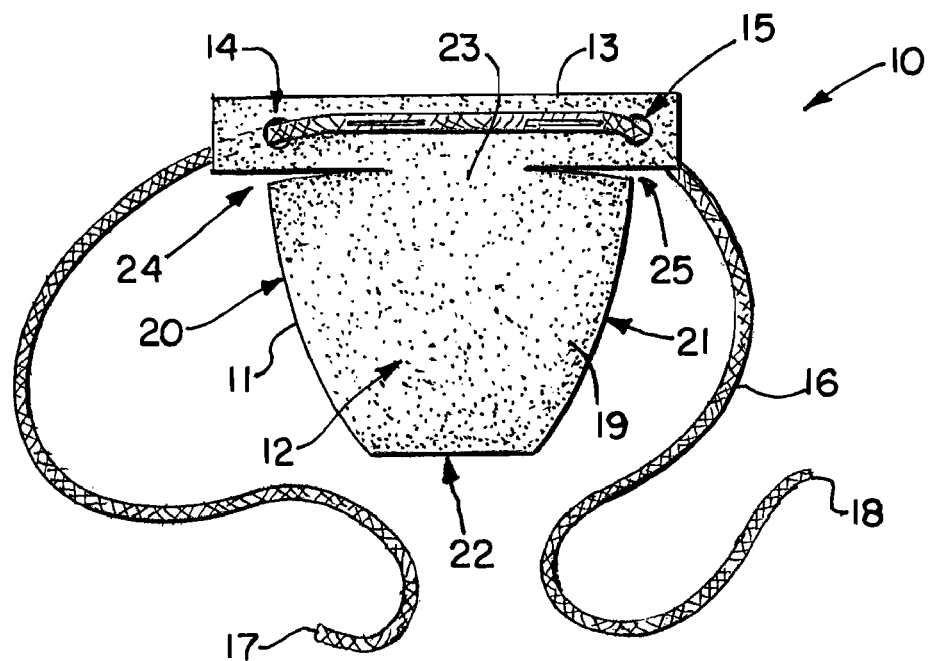
FIG. 1 is a plan view of the preferred embodiment of the apparatus of the present invention showing the tracheotomy tube apparatus planar sheet member in an unfolded generally flat condition.
Figure 2:
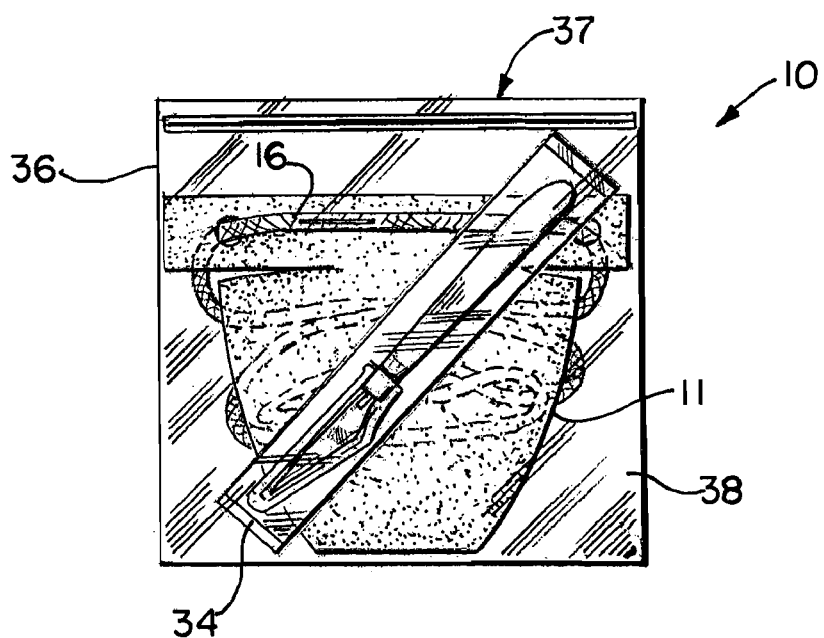
FIG. 2 is a perspective view of the preferred embodiment of the apparatus of the present invention showing the apparatus in storage condition.
Figure 3:
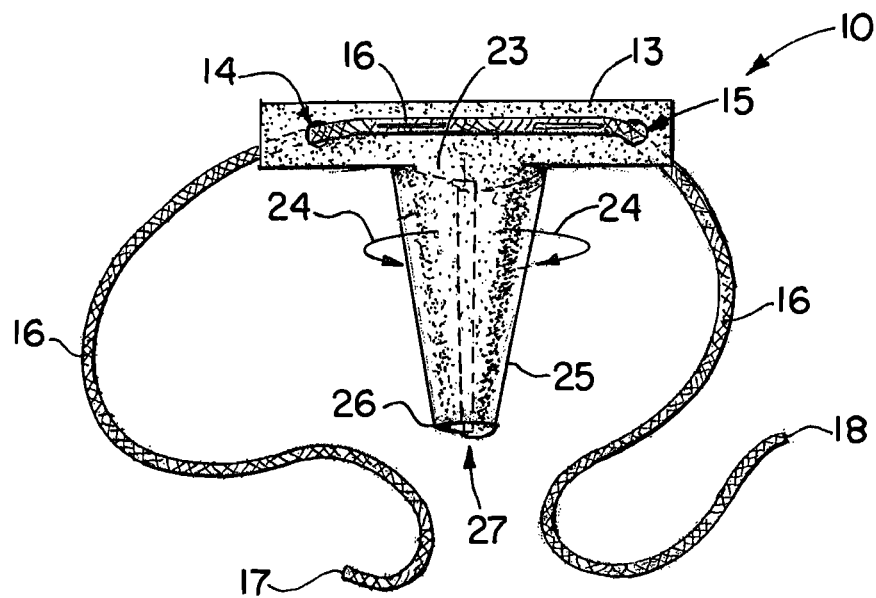
FIG. 3 is a perspective view of the preferred embodiment of the apparatus of the present invention showing the planar sheet member in a rolled or curled position that produces a tubular shape having an open-ended airway.

FIGS. 1-5 show the preferred embodiment of the apparatus of the present invention designated generally by the numeral 10. Tracheotomy tube 10 employs a flat or planar sheet 11. The flat or planar sheet 11 preferably provides at least one surface that is rough or roughened, having for example the texture of a sheet of sandpaper. The sheet 11 provides a generally rectangular section 13 and a tapered section 19. Spaced apart openings 14, 15 are provided in rectangular section 13. Cable 16 is threaded through the openings 14, 15 as shown in FIGS. 1 and 3. Cable 16 has cable ends 17, 18.

Tapered section 19 provides edges 20, 21. As shown in FIG. 1, these edges 20, 21 can be curved. However, they can also be straight. The edges 20, 21 gradually converge as they approach bottom edge 22. Rectangular section 13 and tapered section 19 are joined together at connection 23. Connection 23 can for example be simply a continuation of each of the sections 13, 19 to form a part of sheet 11. In order to form a tube 25 for supplying air to a patient's trachea, the edges 20, 21 are curled toward each other to form a tubular or conical shape shown in FIG. 3 as indicated schematically by arrows 24 in FIG. 3. In this fashion, the edges 20, 21 slightly overlap and because of the roughened surface 12 grip each other at this overlap. The formed tube or cone 25 has an inner end 26 with an opening 27 and an upper end 28 with an opening 29. An open ended bore 31 is thus provided that connects inner end 26 and its opening 27 with upper end 28 and its opening 29. Thus, air flow is continuous through open ended bore 31 during use.

Figure 4:
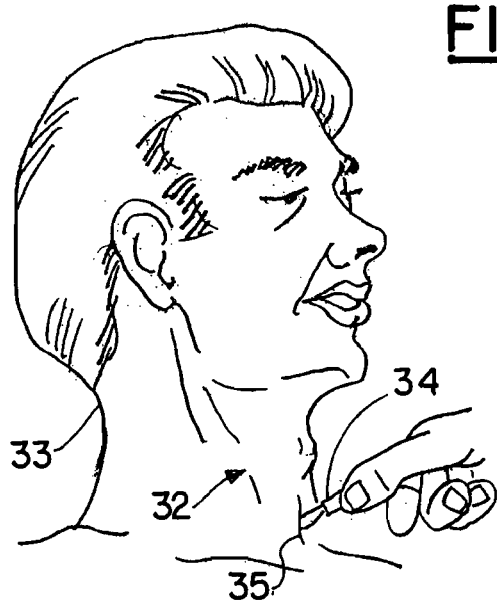
FIGS. 4-5 perspective views of the preferred embodiment of the apparatus of the present invention and showing the method of the present invention and showing attachment to a patient's neck (FIG. 5).
Figure 5:
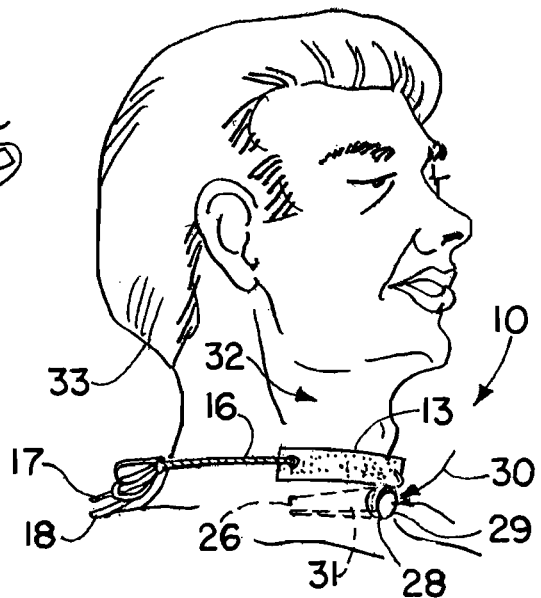

FIGS. 4 and 5 illustrate further the method of the present invention wherein a surgeon prepares a surgically formed opening 35 in the patient's throat area 32 to open the trachea in a manner known to competent surgeons. The patient 34 would thus typically be an individual that is unable to breathe, having his or her trachea blocked by food for example. The formed tube/cone 25 is placed in the surgically formed opening 35 in the position shown in FIG. 5. In this position, the rectangular section 13 conforms to the patient's throat area 32 and cable 16 is tied around the patient's neck as shown in FIG. 5.

The present invention can be contained in a very small package or plastic zipper bag, such as is shown in FIG. 2. The package or zipper bag 36 provides a package interior 38 and a closure 37. The closure 37 could be a zipper type closure such as is found in common food storage bags. The tracheotomy tube 10 of the present invention, an alcohol swab or wipe, and a scalpel 34 can be stored within package 36 interior 38. The alcohol swab could be used to rapidly clean the skin just prior to making the incision of FIG. 4.

Because the combination of package 36, tracheotomy tube 10 and scalpel 34 can be stored substantially flat, the apparatus 10 of the present invention including its package 36 and scalpel 34 can be stored in a user's purse or wallet for emergency use at any time. The tracheotomy tube 10 of the present invention including its package 36, scalpel 34 and tube 10 can be disposable, for a one time use.

The following is a list of parts and materials suitable for use in the present invention.

PARTS LIST

| Part Number | Description |
| --- | --- |
| 10 | tracheotomy tube |
| 11 | flat sheet |
| 12 | rough surface |
| 13 | rectangular section |
| 14 | opening |
| 15 | opening |
| 16 | cable |
| 17 | end |
| 18 | end |
| 19 | tapered section |
| 20 | side edge |
| 21 | side edge |
| 22 | bottom edge |
| 23 | connection |
| 24 | arrow |
| 25 | tube/cone |
| 26 | inner end |
| 27 | opening |
| 28 | upper end |
| 29 | opening |
| 30 | arrow |
| 31 | open ended bore |
| 32 | throat area |
| 33 | patient |
| 34 | scalpel |
| 35 | surgically formed opening |
| 36 | package |
| 37 | closure |
| 38 | package interior |

All measurements disclosed herein are at standard temperature and pressure, at sea level on Earth, unless indicated otherwise. All materials used or intended to be used in a human being are biocompatible, unless indicated otherwise.

The foregoing embodiments are presented by way of example only; the scope of the present invention is to be limited only by the following claims.

The invention claimed is:

1. A tracheotomy tube apparatus, comprising:
   a) a planar sheet member having upper and lower surfaces, at least part of the planar sheet member being flexible so that it can be formed into a tracheal tube shape;
   b) the planar sheet member having a tapered section with a tip and opposed edges that form an acute angle;
   c) the sheet member including a flange having an unattached edge opposite the tip and an edge that connects the flange to the tapered section;
   d) wherein the sheet member occupies a plane in a first, storage position;
   e) a securement for holding the flange to the neck of a patient in a second, operative position; and
   f) a fold that enables the flange to form an angle with a surface of the tapered section in the second, operative position.

2. The tracheotomy tube apparatus of claim 1 wherein the securement is a cable.

3. The tracheotomy tube apparatus of claim 1 wherein the securement is an adhesive.

4. The tracheotomy tube apparatus of claim 1 wherein the tapered section is generally triangularly shaped.

5. A tracheotomy tube apparatus, comprising:
   a) a planar sheet member having upper and lower surfaces, the sheet being flexible so that it can be formed into a tracheal tube shape;
   b) the sheet member having a tapered section with a tip and opposed edges that form an acute angle;
   c) the sheet member having a flange having an unattached edge opposite the tip and an edge that connects the flange to the tapered section;
   d) a securement for holding the flange to the neck of a patient;
   e) a fold that enables the flange to form an angle with a surface of the tapered section; and
   f) wherein there is a slot in between the tapered section and the flange.

6. A tracheotomy tube apparatus, comprising:
   a) a planar sheet member having upper and lower surfaces, the sheet being flexible so that it can be formed into a tracheal tube shape;
   b) the sheet member having a tapered section with a tip and opposed edges that form an acute angle;
   c) the sheet member having a flange having an unattached edge opposite the tip and an edge that connects the flange to the tapered section;
   d) a securement for holding the flange to the neck of a patient;
   e) a fold that enables the flange to form an angle with a surface of the tapered section; and
   f) wherein one of the surfaces is smoother than the other surface.

7. The tracheotomy tube apparatus of claim 6 wherein one of the surfaces is roughened to enable it to grip the surface of a patient's tracheal tissue.

8. A tracheotomy tube apparatus, comprising:
   a) a planar sheet member having upper and lower surfaces, the sheet being flexible so that it can be formed into a tracheal tube shape;
   b) the sheet member having a tapered section with a tip and opposed edges that form an acute angle;

c) the sheet member having a flange having an unattached edge opposite the tip and an edge that connects the flange to the tapered section;
d) a securement for holding the flange to the neck of a patient;
e) a fold that enables the flange to form an angle with a surface of the tapered section; and
f) wherein the planar sheet member has a memory that urges the planar sheet member to return to an original generally flat shape when it is formed into a tubular shape.

9. A tracheotomy tube apparatus, comprising:
a) a planar sheet member having upper and lower surfaces, the sheet being flexible so that it can be formed into a tracheal tube shape;
b) the sheet member having a tapered section with a tip and opposed edges that form an acute angle;
c) the sheet member having a flange having an unattached edge opposite the tip and an edge that connects the flange to the tapered section;
d) a securement for holding the flange to the neck of a patient;
e) a fold that enables the flange to form an angle with a surface of the tapered section; and
f) wherein the planar sheet member has a memory that urges the planar sheet member to return to an original generally flat shape when it is formed into a conical shape.

10. A tracheotomy tube apparatus, comprising:
a) a planar sheet member having upper and lower surfaces, the sheet defining a flat plane when in a first, storage position, the sheet being flexible so that it can be formed into a tracheal tube shape;
b) the sheet having a tracheal tube section that can be rolled into a tubular form having a tip and that provides an open ended airway surrounded by said tracheal tube section to define a second, operative position;
c) the sheet member having a flange having an unattached edge opposite the tip and an edge that connects the flange to the tapered section;
d) a securement for holding the flange to the neck of a patient; and
e) a fold that enables the flange to form an angle with a surface of the tapered section.

11. The tracheotomy tube apparatus of claim 10 wherein the securement is a cable.

12. The tracheotomy tube apparatus of claim 10 wherein the securement is an adhesive.

13. The tracheotomy tube apparatus of claim 10 wherein the tapered section is generally triangularly shaped.

14. A tracheotomy tube apparatus, comprising:
a) a planar sheet member having upper and lower surfaces, the sheet being flexible so that it can be formed into a tracheal tube shape;
b) the sheet having a tracheal tube section that can be rolled into a tubular form having a tip and that provides an open ended airway surrounded by said tracheal tube section;
c) the sheet member having a flange having an unattached edge opposite the tip and an edge that connects the flange to the tapered section;
d) a securement for holding the flange to the neck of a patient;
e) a fold that enables the flange to form an angle with a surface of the tapered section; and
f) wherein there is a slot in between the tapered section and the flange.

15. The tracheotomy tube apparatus of claim 14 wherein there are a pair of slots in between the tapered section and the flange.

16. A tracheotomy tube apparatus, comprising:
a) a planar sheet member having upper and lower surfaces, the sheet being flexible so that it can be formed into a tracheal tube shape;
b) the sheet having a tracheal tube section that can be rolled into a tubular form having a tip and that provides an open ended airway surrounded by said tracheal tube section;
c) the sheet member having a flange having an unattached edge opposite the tip and an edge that connects the flange to the tapered section;
d) a securement for holding the flange to the neck of a patient;
e) a fold that enables the flange to form an angle with a surface of the tapered section; and
f) wherein one of the surfaces is smoother than the other surface.

17. The tracheotomy tube apparatus of claim 16 wherein one of the surfaces is roughened to enable it to grip the surface of a patient's tracheal tissue.

18. The tracheotomy tube apparatus of claim 1 wherein the planar sheet has a memory urges the sheet to return to an original generally flat shape when it is formed into a tubular shape.

19. The tracheotomy tube apparatus of claim 5 wherein there are a pair of slots in between the tapered section and the flange.

20. A tracheotomy tube apparatus, comprising:
a) a planar sheet member having upper and lower surfaces, the sheet being flexible so that it can be formed into a tracheal tube shape;
b) the sheet having a tracheal tube section that can be rolled into a tubular form having a tip and that provides an open ended airway surrounded by said tracheal tube section;
c) the sheet member having a flange having an unattached edge opposite the tip and an edge that connects the flange to the tapered section;
d) a securement for holding the flange to the neck of a patient;
e) a fold that enables the flange to form an angle with a surface of the tapered section; and
f) wherein the planar sheet has a memory urges the sheet to return to an original generally flat shape when it is formed into a conical shape.

\* \* \* \* \*